United States Patent [19]

Freyer et al.

[11] Patent Number: 5,575,653
[45] Date of Patent: Nov. 19, 1996

[54] ARTIFICIAL TOOTH BLANK MADE IN SERIES PRODUCTION

[75] Inventors: Martha Freyer; Rainer Mattern, both of Bad Säckingen, Germany

[73] Assignee: Vita Zahnfabrik H. Rauter GmbH & Co. KG, Bad Sackingen, Germany

[21] Appl. No.: 41,655

[22] Filed: Apr. 1, 1993

[30] Foreign Application Priority Data

Apr. 1, 1992 [DE] Germany .......................... 42 10 781.4

[51] Int. Cl.⁶ .................................................. A61C 5/08
[52] U.S. Cl. ................ 433/202.1; 433/206; 433/212.1; 433/222.1; 264/16; 264/19; 264/20; 264/138; 264/139; 428/469; 428/472; 428/701; 428/702
[58] Field of Search .................... 428/457, 469, 428/472, 701, 702, 699, 657; 433/212.1, 202.1, 206, 222.1; 264/16, 19, 20, 138, 139

[56] References Cited

U.S. PATENT DOCUMENTS

| | | | |
|---|---|---|---|
| 3,621,576 | 11/1971 | Gnecco | 32/8 |
| 4,104,798 | 8/1978 | Takahashi et al. | 32/12 |
| 4,145,764 | 3/1979 | Suzuki et al. | 3/1.9 |
| 4,187,608 | 2/1980 | Nyce | 433/201 |
| 4,431,451 | 2/1984 | Mabie et al. | 433/222 |
| 4,437,192 | 3/1984 | Fujiu et al. | 428/432 |
| 4,556,389 | 12/1985 | Ueno et al. | 428/469 |
| 4,557,691 | 12/1985 | Martin | 433/228.1 |
| 4,671,770 | 6/1987 | Bell et al. | 433/223 |
| 4,684,555 | 8/1987 | Neumeyer | 428/469 |
| 4,744,759 | 5/1988 | Bowen | 433/228.1 |
| 4,970,032 | 11/1990 | Rotsaert | 433/202.1 |
| 5,346,397 | 9/1994 | Braiman | 433/212.1 |

FOREIGN PATENT DOCUMENTS 371862 9/1963 Switzerland.

*Primary Examiner*—Archene Turner
*Attorney, Agent, or Firm*—Jacobson, Price, Holman & Stern, PLLC

[57] ABSTRACT

The artificial tooth blanks made by series production involve a dentin-colored fired dental ceramic composition including a previously compression-molded hard core and optionally a retention, wherein the size of the artificial tooth blank is reduced over that of the corresponding finished artificial tooth and the artificial tooth blanks do not contain an enamel layer. The retention may involve one or more high-melting shells incorporated by firing and containing high-melting retention pins soldered therein after firing, wherein the retention pins as well as the solder are stable under the melting conditions for dental ceramic compositions for bridges and crowns, and especially so in the presence of air as well.

14 Claims, No Drawings

ARTIFICIAL TOOTH BLANK MADE IN SERIES PRODUCTION

The present invention relates to an artificial tooth blank including a dentin-colored fired dental ceramic composition including a pre-fired hard core and a retaining means ("retention").

Artificial teeth are manufactured in various shapes and colors as well as of a variety of materials. Whereas teeth made of synthetic materials (plastics) in general are bonded to the base material by polymerization and cross-linking, artificial teeth made of fired ceramic compositions in general need a retaining means. The retaining means, the so-called retention, in the simplest case consists of a stable adhesion bond. However, it is preferred to use additional fixing devices. While molars often comprise an undercut retention opening with one or two fine deaerating channels, especially front teeth are furnished with one or two retention pins. This is done, for example, by inserting a metal shell into the green ceramic mass, said mass additionally comprising an outer bulge which will firmly anchor the shell in the fired ceramic composition. The retention pins later on will be soldered into said shells. These in most cases consist of a nickel alloy coated with a thin gold layer. For soldering, a suitable solder and the pin are inserted into the shell, and then the already fired artificial teeth are heated in an oven at temperatures where the solder melts. After cooling, these pins have been well and durably bonded to the shell.

In order to achieve a permanent fixture of the shell in the ceramic composition it has proven to be useful that said shells are included in the still unfired ceramic composition in dentin color. In some artificial teeth, the ceramic composition in dentin color consists of a back or cervical mass stained somewhat darker and a dentin mass stained somewhat brighter towards the tooth front. Nevertheless, there are already many cases where such a differentiation is abandoned, so that back and cervical mass and the mass present towards the front consist of the same material. Towards the front side this is covered by a transparent enamel composition. The latter in general consists of the same ceramic material, however without any opacifying additives. The mold cavities for the front sides of the teeth filled with the unfired ceramic compositions are pressed against the matching mold cavities appropriately filled for the reverse side—if so desired, already having a hard core with shell inserted—and the resulting assemblies are dried at an elevated temperature. The obtained dried blanks are inspected, cleaned and fired at temperatures between 1100° C. Then the retention pins are soldered into the completely fired artificial teeth.

The undercut holes with the deaeration channels of the molar teeth are in general produced by inserting conical wooden pegs which will completely burn off during the firing step.

Now, due to the recent development of high-quality adhesives and adhesive compositions, in the meantime it has become basically possible to omit said retention pins and retention holes, respectively, and to attach the artificial teeth made of fired ceramic material to the base material by adhesion-bonding. However, hitherto this method has not been employed in practice.

One substantial drawback inherent in all artificial teeth made of fired dental ceramic compositions as obtained by series production resides in that a considerable multiplicity of various shapes and colors must be provided in order to be able to select artificial teeth suitable for a patient's type and, possibly, matching with the remaining patient's own natural teeth. In spite of the variety of artificial teeth that has been available in the market for years, there is an increasing demand for further variants with respect to shape and color of the artificial teeth. The patients as well as the dentists and dental technicians express their desire for a more individual design of dental prostheses such as to offer optimum aesthetics and function. Such an extension of the offered collection is hardly possible, and nobody would want to assume a responsibility for the increase of costs of the molds, stock keeping and sales expenditure. Thus, there is a problem of keeping the costs of artificial teeth as low as possible, on the one hand, and to provide the artificial teeth in the largest possible variety of shapes and colors, on the other hand.

This problem can be solved in a surprisingly easy way be providing an artificial tooth blank made by series production, which comprises a dentin-colored fired dental ceramic composition including a previously compression-molded hard core and a retention, characterized in that the size of the artificial tooth blank is reduced over that of the corresponding finished artificial tooth and that the artificial tooth blank does not comprise an enamel layer. The dental technician can apply onto this artificial tooth blank both dentin mass or an enamel layer made of dental ceramic compositions, which hitherto have only been used for bridges and crowns. These dental ceramic compositions are generally fired at temperatures of from 900° C. to 960° C. If said compositions are applied onto the artificial tooth blank according to the invention, a permanent bond is formed upon burning between the two different dental ceramic compositions, especially so, if the surface of the artificial tooth blank is artificially roughened prior to the application. Since the size of the artificial tooth blank has been reduced over that of the final artificial tooth, the dental technician is enabled to apply and bake an opacified dentin mass as well as transparent enamel layers made of dental ceramic compositions. The artificial tooth obtained thereby, thus, is very individually designed and formed and adapted to the particular needs with respect to its shape and color. The mechanical durability of these dental ceramic compositions for bridges and crowns when fired is well comparable to the wear resistance of artificial teeth as so far known made of dental ceramic compositions.

A particular problem is associated with the front teeth which preferably comprise a retention consisting of one or more shells incorporated by firing and retention pins soldered therein. Namely, these will have to be present already in the artificial tooth blank according to the invention, because it cannot be expected that the dental technician would solder such retention pins in the shells. However, the retention pins made of a gold-plated nickel alloy as in use hitherto, on the one hand, and the solder used for soldering these pins, on the other hand, are unsuitable, since they are not capable to stand the conditions of subsequently firing the dental ceramic compositions for bridges and crowns. Thus, it is necessary that for such retentions both the retention pins and the solder are stable under the melting conditions for dental ceramic compositions for bridges and crowns, and especially so in the presence of air as well. Thus, the solder should not melt below 1000° C. The retention pins also should neither melt nor oxidize at 1000° C. in air. In this respect, platinum has proven to be particularly suitable. However, pins made of platinum-plated titanium could basically be used as well.

The retention, however, may also consist of one or more pre-fabricated high-melting retentive ceramic parts. Suitable are, for example, ceramic pins made of alumina or of zirconia-reinforced alumina.

As artificial teeth made from the artificial tooth blanks according to the invention in combination with subsequently applied dental ceramic compositions for bridges and crowns can be very individually designed with respect to shape and color, the needs of patients, dentists and dental technicians can be fully satisfied. On the other hand, the artificial tooth blanks will have to be provided only in a few sizes, types and colors.

While hitherto attempts have always been made to satisfy the increasing demands for artificial teeth by enlarging the assortment offered, by means of the artificial tooth blank according to the invention it becomes possible to significantly reduce the assortment with respect to sizes and colors. Crucial for this result was the reduction in size of the artificial tooth blank over that of the previous complete artificial teeth, the omission of the enamel layer and, for teeth which comprise shells incorporated by firing and retention pins attached by soldering, the adequate adaption to the changed needs of the material for the retention pins as well as the solder material. It was certainly not obvious now no longer to provide the artificial teeth supplied hitherto in the final ready-to-use condition, but instead to transfer the entire individual adaption to the dental technician's workshop, although the manpower of a dental technician certainly will be more expensive than the large series production of finished artificial teeth. However, this transfer in a technically unobjectionable manner allows compliance with the increased demands for further variants in shape and color of the artificial teeth. The transfer to the dental technician's workshop has become possible only after dental ceramic compositions for bridges and crowns have been made available which, when fired at 900° C. to 960° C., have mechanical properties comparable to those of artificial teeth made of fired ceramic compositions which are fired at from 1100° C. to 1350° C. However, care is to be taken that these dental ceramic compositions for bridges and crowns will be firmly bonded to the artificial tooth blanks and that the expansion coefficients are at least very similar. Thus, dental ceramic compositions for bridges and crowns to be applied to metal alloys are less suitable. However, well suitable are the compositions that, for example, are used for coating fired ceramic compositions and which are provided by Vita Zahnfabrik H. Rauter GmbH & Co. KG under the designation VITADUR N. It is of course also possible, in one dental prosthesis to combine conventional artificial teeth with artificial teeth made of artificial tooth blanks according to the invention and fired coatings made of dental ceramic compositions for bridges and crowns.

What is claimed is:

1. The method of making a tooth blank for an artificial tooth comprising compression-molding and firing a dentin-colored dental ceramic to a retention, such that the tooth blank is smaller than the artificial tooth and bondable to at least one enamel layer to form the artificial tooth.

2. The method of claim 1 wherein the retention comprises at least one shell and, optionally, at least one pin fixed to the shell after compression-molding and firing, wherein the retention is stable at temperatures of 900°–960° C.

3. The method of claim 1 wherein the at least one enamel layer comprises a fired ceramic composition useful for bridges or crowns.

4. A method of making an artificial tooth comprising making a tooth blank according to claim 1 followed by fire-bonding to the tooth blank a composition useful for bridges or crowns to form the enamel layer.

5. A tooth blank, useful for making an artificial tooth having an outer enamel-layer, comprising (a) a core of a compression-molded and fired dentin-colored dental ceramic and (b) a retention that is fixed to the core and is capable of anchoring the tooth blank to a substrate, wherein the tooth blank does not include, but can accommodate, the outer enamel layer.

6. The tooth blank of claim 5 wherein the retention is stable under conditions necessary to fire-bond to the tooth blank a ceramic composition useful for bridges or crowns.

7. The tooth blank of claim 6 wherein the retention comprises at least one shell fixed to the core and at least one pin that protrudes from the tooth blank and is fixed to the shell.

8. The tooth blank of claim 1 wherein the retention is stable at temperatures of 900° to 960° C.

9. The tooth blank of claim 5 wherein the retention is stable at temperatures of 900° to 960° C.

10. An artificial tooth comprising (a) a pre-formed tooth blank comprising a core of compression-molded and fired dentin-colored dental ceramic and a retention that is fixed to the ceramic and is capable of anchoring the artificial tooth to a substrate, and (b) an outer enamel layer fixed to the pre-formed tooth blank.

11. The artificial tooth of claim 10 wherein the outer enamel layer comprises a ceramic composition useful for bridges or crowns fixed to the pre-formed tooth blank by fire-bonding and wherein the retention is stable under conditions necessary for the fire-bonding.

12. The artificial tooth of claim 11 wherein the retention comprises at least one shell fixed to the core and at least one pin that protrudes from the tooth blank and is fixed to the shell.

13. The artificial tooth of claim 12 wherein the retention is stable at temperatures of 900°–960° C.

14. The artificial tooth of claim 10 wherein the retention is stable at temperatures of 900°–960° C.

* * * * *